United States Patent [19]
Galoian et al.

[11] 3,944,665
[45] Mar. 16, 1976

[54] NOVEL BIOLOGICALLY-ACTIVE COMPOUNDS AND METHOD FOR ISOLATING THEM FROM RAW MATERIALS CONTAINING INSULIN

[76] Inventors: Armen Anushavanovich Galoian, ulitsa Ter-Gabrielyana, 2, kv. 66; Ruben Arshakovich Alexanian, ulitsa Moskovskaya, 60, kv. 29; Mavra Vagarshanovna Oganian, ulitsa Orbeli, 7, kv. 39, all of Erevan, U.S.S.R.

[22] Filed: Jan. 22, 1974

[21] Appl. No.: 435,469

[30] Foreign Application Priority Data
Feb. 15, 1973   U.S.S.R. .............................. 1882646

[52] U.S. Cl. ............................... 424/101; 424/110
[51] Int. Cl.$^2$ .......................................... A61K 27/00
[58] Field of Search .......................... 424/101, 110

[56] References Cited
UNITED STATES PATENTS

| | | | |
|---|---|---|---|
| 2,424,401 | 7/1947 | Lesuk | 424/110 |
| 2,784,142 | 3/1957 | Schultz | 424/110 |

*Primary Examiner*—Frederick E. Waddell

[57] ABSTRACT

The biologically-active compounds disclosed herein are two low-molecular water-soluble compounds that are formed in the incretory apparatus of the pancreas, which exhibit a coronary dilating effect and which are characterized by the following physico-chemical and biological properties, on chromatograms with a butyl alcohol-acetic acid-water (4:1:5) solvent system, the distribution coefficient Rf for these compounds is 0.45 and 0.6, respectively; in an electrophoretic field of 1500 v, at a pH of 3.8, an ionic strength of 0.1 and a current density of 1.2 mA/cm, one of these compounds moves toward the cathode (−6 cm) and the other towards the anode (+4 cm); they may be dialyzed through a semi-permeable membrane; they do not affect the glucose level of blood during their intravenous administration; the molecular weights according to the chromatographic, electrophoretic and gel filtration data is from 300–400 and from 200–300, respectively.

The method for isolating the said compounds from insulin-containing raw materials consists in that the serum of the venous blood of the pancreas is dialyzed against a 2N solution of acetic acid at a temperature of 3°–10°C for from 24–48 hours, the dialyzate is lyophilized, and the end products are finally isolated from the dialyzate by gel filtration, chromatography and electrophoresis.

3 Claims, No Drawings

NOVEL BIOLOGICALLY-ACTIVE COMPOUNDS AND METHOD FOR ISOLATING THEM FROM RAW MATERIALS CONTAINING INSULIN

This invention relates to novel biologically-active compounds and a method for isolating them from raw materials containing insulin.

According to the invention the novel biologicallyactive compounds are two low-molecular water-soluble substances that are formed in the incretory apparatus of the pancreas and which exhibit a coronary-dilating effect, and which are characterized by the following biological and physico-chemical properties: on chromatograms with a butyl alcohol-acetic acid-water (4:1:5) solvent system, the coefficient of distribution of these compounds Rf is 0.45 and 0.6, respectively; in the electrophoretic field of 1500 v at a pH of 3.8, an ionic strength of 0.1 and a current density of 1.2 mA is exhibited; one of these compounds moves toward the cathode (−6 cm), while the other toward the anode (+4cm); they may be dialyzed through a semi-permeable membrane; they do not change the glucose level in the blood during their intravenous administration; the molecular weight according to chromatographic, electrophoretic and gel filration data are from 300 − 400 and from 200 − 300, respectively.

These said, compounds are coronary dilating agents and can therefore be used in medicine. A physiological solution of the biologically-active compounds was administered intravenously to a cat and the volume of the cardiac blood flow was measured. The volume of the venous discharge from the heart increased 250 per cent 10 to 15 minutes after the intravenous administration of the preparation and persisted for from 1–2.5 hours, with the arterial pressure remaining practically unchanged during the entire experiment.

An intensification of the coronary blood flow is also corroborated by the results of experiments with radio-active isotopes. Radio-active iodine ($Na^{131}$) was administered into the region of the experimental myocardial infarction in a dog. The descending branch of the left-hand coronary artery was tied up and the time during which the radioactive iodine was removed from the tied portion was measured. The administration of the biologically-active substances markedly increased the rate of discharge of the radioactive iodine from the blood vessels.

The proposed biologically-active substances are formed in the insular apparatus of the pancreas. This has been proven by the following fact. If the insular apparatus is affected by alloxane, the excretion of the said substances is either markedly inhibited or discontinues altogether.

When the sinus nerves are cut and the anterier hypothalamus mechanically destroyed (experiments on 50 cats), the biologically-active substances prove ineffective. These data indicate that the said substances do not exert any direct effect on the coronary circulation, but act through the stimulation of the coronary-dilating hormone excretion from the hypothalamus. The proposed novel substances do not affect the glucose level in the blood during their intravenous administration.

The method for isolating the said biologically-active compounds from insulin-containing material consists in that the serum of the venous blood of the pancreas is dialyzed against a 2N solution of acetic acid at a temperature of 3–10°C for from 24–48 hours, the dialyzate is then lyophilized, and the end products are finally isolated by chromatography, electrophoresis and gel filtration.

The proposed method is carried out as follows.

The serum of the venous blood of the pancreas containing insulin is used as the starting material. The serum is dialyzed against a 2N solution of acetic acid at a temperature of 3°–10°C for from 24–48 hours. The obtained dialyzate is lyophilized and the end products are finally isolated from the lyophilizate by gel filtration. Gel filtration is performed on a column with Sephadex packing (pore size 200 − 400 $\mu$). A phosphate buffer (0.067M) is used as the elution agent. The components are separated by down-flow papers chromatography with a butyl alcohol-acetic acid-water solvent system (taken in the ratio of 4:1:5). Next, a high-voltage paper electrophoresis is carried out in a citrate buffer at a pH of 3.8, at 1500 v, an ionic strength of 0.1, and a current density of 1.2 mA/cm for 3.5 hours in order to isolate the end products which are two low-moleculr water-soluble compounds having the following biological and physico-chemical low-molecular on chromatograms with the above specified solvent system, the distribution coefficient Rf for these compounds is 0.45 and 0.6, respectively; in an electrophoretic field of 1500 v. at an ionic strength of 0.1 and a current density of 1.2 mA/cm, one of these compounds moves toward the cathode (−6 cm), and the other toward the anode (+4 cm); they may be dialyzed through a semi-permeable membrane; they exhibit coronary dilating effect, and do not change the glucose level in the blood during their intravenous administration; and the molecular weight of one compound is from 300 − 400 and of the other from 200 − 300.

For a better understanding of the invention, the following example of its practical embodiment is given by way of illustration.

EXAMPLE 10 ml of venous blood serum from the pancreas is placed into a semi-permeable material bag and immersed into a vessel containing 50 ml of a 2N solution of acetic acid. Dialysis is carried out at a temperature of 4°C with stirring for 24 hours. The medium (2N solution of acetic acid) is changed twice. The dialyzates are added and lyophilzed. The lyophilizate thus obtained is subjected to gel filtration in order for the end products to be separated. Gel filtration is effected on a column packed with Sephadex (pore size 200 − 400 micron). The elution agent is 0.067M of a phosphate buffer. The separation of the components is effected by paper chromatography with a butyl alcohol-acetic acid-water (4:1:5) solvent system. This is followed by high-voltage paper electrophoresis in a citrate buffer (pH 3.8 ) at 1500 v, having an ionic strength of 0.1, and a current density of 1.2 mA/cm for 3.5 hours. The biologically-active compounds of the present invention are separated as a result.

The coronary dilating effect of these compounds has been tested on the coronary circulation of a cat by the Moravitz and Zahn method. The venous discharge from the heart vessels per unit time increases 250 per cent. The coronary dilating effect persists for 2.5 hours, the arterial pressure remaining unaltered during the course of the experiment.

The distribution coefficient Rf for these substances on chromatograms with a butyl alcoholacetic acid-water (4:1:5) solvent system is 0.45 to 0.6, respectively. In the electrophoretic field of 1500 v, at a pH of 3.8, an ionic strength of 0.1 and a current density of 1.2 mA/cm, one of these compounds moves toward the cathode (−6 cm) and the other toward the anode (+4 cm).

The molecular weight, according to chromatographic, electrophoretic and gel filtration data, is from 300–400 and from 200–300, respectively.

What is claimed is:

1. A method of isolating biologically-active compounds which exhibit a coronary dilating effect from the venous blood of the pancreas comprising dialyzing the serum of the venous blood of the pancreas against a 2N solution of acetic acid at a temperature of 3–10°C for from 24 to 28 hours, lyophilizing the dialyzate, gel filtering the lyophilizate on a column with packing having a pore size of 200–400m$\mu$, and separating said compounds from each other by down-flow paper chromatography using said butyl alcohol-acetic acid-water solvent system in a ration of 4:1:5 followed by high voltage paper electrophoresis in an electrophoretic field of 1,500 volts in a citrate buffer, at an ionic strength of 0.1 and a current density of 1.2 mA/cm.

2. A biologically-active low-molecular weight water-soluble compound which is prepared by the method of claim 1, which compound exhibits a coronary dilating effect and is characterized by the following biological and physical-chemical properties:
   A. on chromatograms with a butyl alcohol-acetic acid-water solvent system taken in the ratio of 4:1:5, the coefficient of distribution Rf is 0.45;
   B. in an electrophoretic field of 1,500 v, at a pH of 3.8, an ionic strength of 0.1, and a current density of 1.2 mA/cm, said compound moves toward the cathode (−6 cm);
   C. it is dialyzable through a semi-permeable membrance;
   D. it does not change the glucose level of blood as it is intravenously administered;
   E. and the molecular weight is from 300 to 400.

3. A biologically-active low-molecular weight water-soluble compound which is prepared by the method of claim 1, which compound exhibits a coronary dilating effect and is characterized by the following biological and physical-chemical properties:
   A. on chromatograms with a butyl alcohol-acetic acid-water solvent system taken in the ratio of 4:1:5, the coefficient of distribution Rf is 0.6;
   B. in an electrophoretic field of 1,500 v, at a pH of 3.8, an ionic strength of 0.1, and a current density of 1.2 mA/cm, said compound moves toward the anode (+4 cm);
   C. it is dialyzable through a semi-permeable membrane;
   D. it does not change the glucose level of blood as it is intravenously administered;
   E. and the molecular weight is from 200 to 300.

* * * * *